United States Patent
Zhang et al.

(10) Patent No.: US 11,331,024 B2
(45) Date of Patent: May 17, 2022

(54) CALIBRATION METHOD FOR CRITICAL POINT OF MENTAL FATIGUE BASED ON SELF-ORGANIZED CRITICALITY

(71) Applicant: DALIAN UNIVERSITY OF TECHNOLOGY, Liaoning (CN)

(72) Inventors: Chi Zhang, Liaoning (CN); Ying Li, Liaoning (CN); Fengyu Cong, Liaoning (CN); Hanbing Gao, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 17/416,182

(22) PCT Filed: Aug. 18, 2020

(86) PCT No.: PCT/CN2020/109699
§ 371 (c)(1),
(2) Date: Jun. 18, 2021

(87) PCT Pub. No.: WO2022/027730
PCT Pub. Date: Feb. 10, 2022

(65) Prior Publication Data
US 2022/0039716 A1 Feb. 10, 2022

(30) Foreign Application Priority Data
Aug. 7, 2020 (CN) .......................... 202010786246.1

(51) Int. Cl.
*A61B 5/16* (2006.01)
*A61B 5/369* (2021.01)

(52) U.S. Cl.
CPC .............. *A61B 5/165* (2013.01); *A61B 5/369* (2021.01); *A61B 2560/0223* (2013.01)

(58) Field of Classification Search
CPC ........ A61M 2230/005; A61M 2230/06; A61M 2230/20; A61K 39/3955; A61K 2300/00; A61B 5/0006; A61B 5/369
See application file for complete search history.

(56) References Cited

U.S. PATENT DOCUMENTS

| 10,580,142 B1 | 3/2020 | Hoffmann et al. |
| 2016/0270718 A1* | 9/2016 | Heneghan ......... A61M 16/0069 |

(Continued)

FOREIGN PATENT DOCUMENTS

| CN | 102722727 A | 10/2012 |
| CN | 109770923 A | 5/2019 |

(Continued)

OTHER PUBLICATIONS

Chialvo, Dante R., "Emergent complex neural dynamics: the brain at the edge," Nature Physics vol. 6, Oct. 31, 2010, pp. 744-750.
(Continued)

*Primary Examiner* — Christine H Matthews
*Assistant Examiner* — Joshua D Lannu
(74) *Attorney, Agent, or Firm* — Muncy, Geissler, Olds & Lowe, P.C.

(57) ABSTRACT

The present invention belongs to the technical field of processing and analysis of biomedical signals, and provides a calibration method for the critical point of mental fatigue based on self-organized criticality. It constructs a self-organized criticality model by using the dynamic characteristics of a brain network, and deduces the avalanche dynamics of mental fatigue, which is consistent with the internal mechanism of evolution of fatigue complexity. The critical state of calibration is dynamically stable and robust. Through the verification of the behavior data, the reliability of the critical state of mental fatigue determined from physiological and behavioral dimensions is high, providing (Continued)

support for the setting of the fatigue category labels to complete more accurate classification and recognition.

2 Claims, 3 Drawing Sheets

(56) References Cited

U.S. PATENT DOCUMENTS

2020/0110111 A1    4/2020   Chueng et al.
2020/0337645 A1*  10/2020  Kremen ................ A61B 5/374

FOREIGN PATENT DOCUMENTS

| CN | 110151203 A | 8/2019 |
| CN | 110338785 A | 10/2019 |
| CN | 110353666 A | 10/2019 |

OTHER PUBLICATIONS

Shew, Woodrow L, et al. "Adaptation to sensory input tunes visual cortex to criticality," Nature Physics, vol. 11, Aug. 31, 2015 659-664, Macmillan Publishers Limited.

Luo, Yan, "Impact of Sleep Deprivation on Neuronal Avalanche of Rat Default Mode Network," A Master Thesis Submitted to University of Electronic Science and Technology of China, Discipline: Biomedical Engineering, School: School of Life Science andTechnology, May 29, 2019, 62 pages.

* cited by examiner

CALIBRATION METHOD FOR CRITICAL POINT OF MENTAL FATIGUE BASED ON SELF-ORGANIZED CRITICALITY

TECHNICAL FIELD

The present invention belongs to the technical field of processing and analysis of biomedical signals. From the perspective of electrophysiology, it mainly proposes a calibration method for the critical point of mental fatigue based on self-organized criticality.

BACKGROUND

With the rapid development of the society, the pressure of work and study has been heavily increased. Prolonged work and study will lead to drowsiness, unconsciousness, sluggishness and other symptoms of mental fatigue. For personnel in some special industries, such as coach drivers and pilots, mental fatigue will affect the ability to drive, mainly manifested as distraction, dozing, narrowing of vision and slow reaction and judgment, which may seriously pose a threat to driving safety. Therefore, it is of great practical significance to identify meaningful fatigue index and detect mental fatigue for improving the continuous working ability of the special workers and ensuring their safety.

Electroencephalograph (EEG) records electrical activities in the regions between pairs of electrodes on the scalp. These electrical activities represent the sum of the electrical activities of a large number of neurons inside the brain around the electrodes, and can reflect the interaction and information communication state of functional regions of the brain. At present, EEG signals have been proved by massive studies to be the most potential and reliable measure of mental fatigue. However, the existing EEG-based detection methods are not satisfactory in the practical application process, and many problems need to be solved. For example, detection indexes are inevitably interfered by various external factors. Especially, EEG has low signal-to-noise ratio and spatial resolution, and is easy to cause signal mixing problems. For continuous tasks, the complexity of the environment and the dynamic changes of task demands make it difficult to calibrate the critical points of fatigue and accurately distinguish different states of operators. In order to effectively promote the detection techniques of mental fatigue, there is an urgent need to introduce an internal mechanism of fatigue complexity evolution to improve the reliability of the calibration for the critical points of fatigue.

SUMMARY

Aiming at the problems and challenges above, the present invention proposes a calibration method for the critical point of mental fatigue based on self-organized criticality, so as to deduce avalanche dynamics of mental fatigue by a self-organized criticality model, to calibrate the critical point of mental fatigue and to distinguish the mental fatigue state. The self-organized criticality is an intrinsic property of a system, and not affected by the external control parameters of the system, i.e., a self-organized criticality state is dynamically stable and robust. The self-organized criticality is applied to the calibration of the critical point of mental fatigue to form a fatigue state distinguishing method independent of the initial state and external parameter control, which is conducive to early analysis and judgment of fatigue at the critical point and the setting of fatigue category labels to complete more accurate classification and recognition.

The technical solution of the present invention is as follows:

The calibration method for the critical point of mental fatigue based on self-organized criticality comprises the following steps:

Step 1: according to the international standard 10-20 electroencephalograph (EEG) electrode placement system, collecting EEG signals in the specific prolonged operation process like driving, simultaneously collecting operation behavior data and conducting data preprocessing on the EEG signals;

Step 2: constructing a dynamic functional brain network by using a sliding time window, and analyzing statistical characteristics of the dynamic functional brain network;

analysis of the dynamic functional brain network comprises:

calculating the correlation coefficients between the EEG data of each channel in the sliding time window to obtain an adjacency matrix;

establishing a weighted brain network with EEG electrodes as nodes and adjacency matrix elements as edges;

calculating the maximum threshold that makes the weighted brain network become a connected graph, and binarizing the adjacency matrix to establish a binary brain network;

analyzing the statistical characteristics of the binary brain network, and extracting the statistical characteristics of clustering coefficient, characteristic path length and global efficiency;

Step 3: deducing the avalanche dynamics of mental fatigue on the dynamic functional brain network, constructing the self-organized criticality model by particle addition and particle collapse processes, judging whether the brain network has self-organized criticality and detecting the critical state of mental fatigue;

detection of the critical state of mental fatigue based on the self-organized criticality model comprises:

integrating clustering coefficient, characteristic path length and global efficiency, and calculating the fatigue index of the dynamic functional brain network to obtain the dynamic characteristics of the brain network;

adding particles to the nodes of the brain network according to degree distribution, and increasing the height of the nodes by 1 after adding the particles;

setting the collapse height threshold of each node to be the same as the degree of the node, and judging the collapse;

recording the stability of all the nodes after the collapse as an avalanche, and deducing the avalanche dynamics;

detecting whether the brain network has self-organized criticality based on that an avalanche behavior of self-organized criticality has "power law" distribution;

calibrating the self-organized critical point by using the "power law" distribution law of the avalanche behavior;

Step 4: inspecting the validity of calibration of the critical point of mental fatigue based on the self-organized criticality in combination with the operation behavior data of the specific work;

realizing inspection of the calibration validity of the fatigue critical point through behavior data characteristic extraction, and judging whether the behavior data characteristic outliers appear near the critical point.

Further, for the behavior data characteristic extraction, an analysis algorithm comprises:

standardizing the behavior data based on Z-score;

fusing the behavior data by a weighted average method;

calculating the mean, standard deviation and sample entropy of the behavior data as characteristic values.

The beneficial effects of the present invention includes that: it proposes the calibration method fir the critical point of mental fatigue based on self-organized criticality, so as to construct the self-organized criticality model by using the dynamic characteristics of the brain network, and to deduce the avalanche dynamics of mental fatigue, which is consistent with the internal mechanism of evolution of fatigue complexity. The critical state of calibration is dynamically stable and robust. Through the verification of the behavior data, the reliability of the critical state of mental fatigue determined from physiological and behavioral dimensions is high, providing support for the setting of the fatigue category labels to complete more accurate classification and recognition.

DETAILED DESCRIPTION

To deepen its understanding, the present invention will be further described below in detail in combination with figures and embodiments. The embodiments do not have a limitation to the protection scope of the invention.

Figure 1:
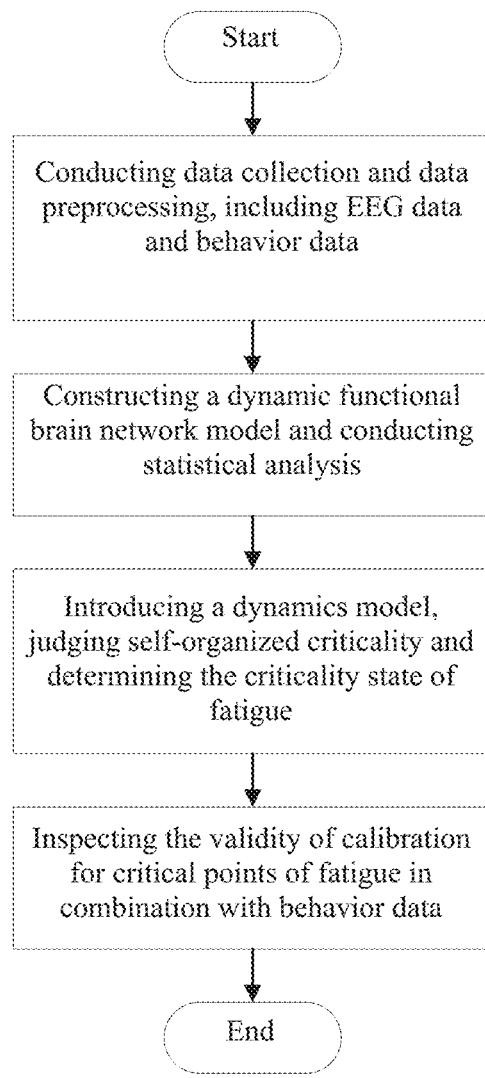
FIG. 1 is a flow chart of a calibration method for the critical point of fatigue based on self-organized criticality.
Figure 2:
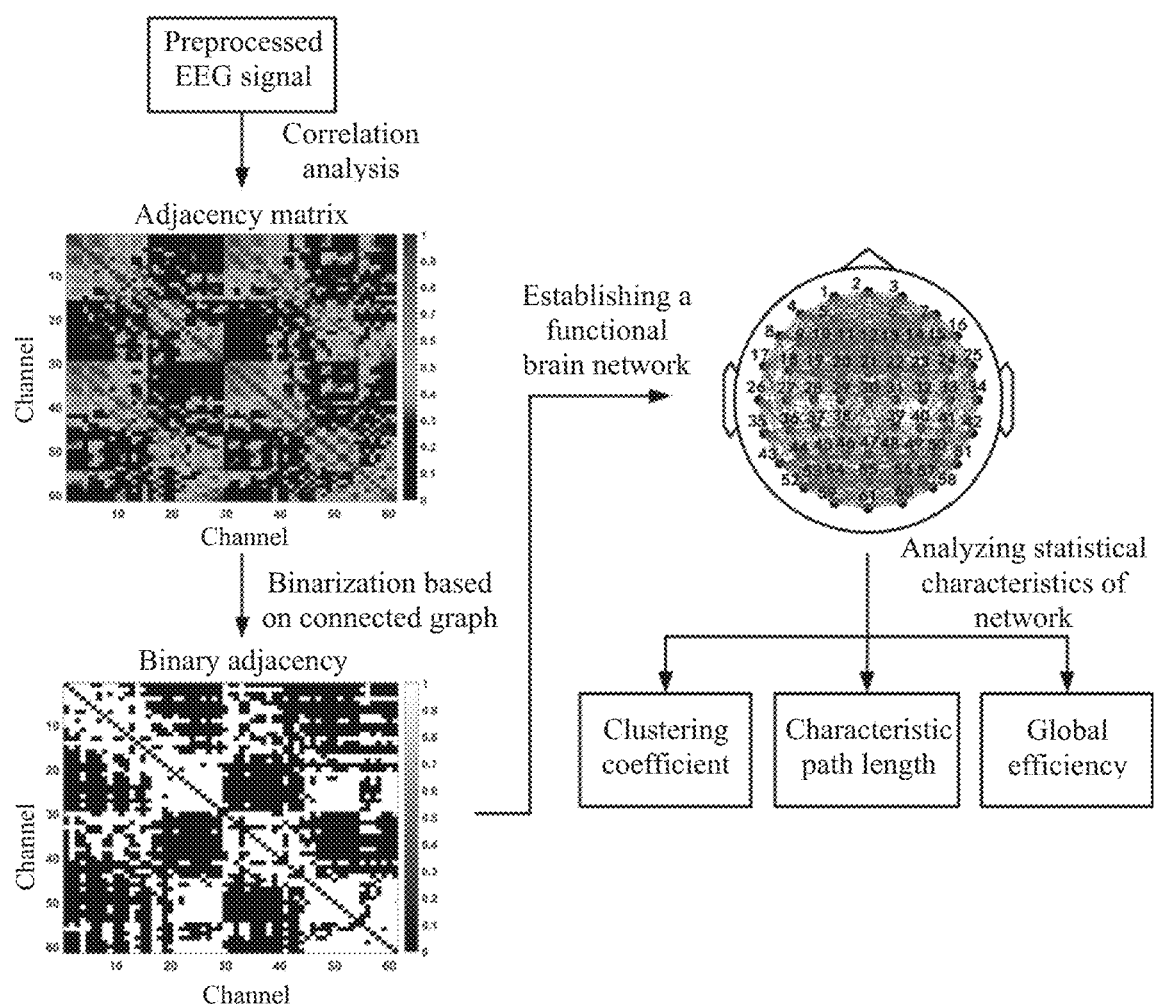
FIG. 2 is a technology roadmap of extraction of statistical characteristics of a dynamic functional brain network in the present invention.

Referring to FIG. 1, the embodiment provides a calibration method for the critical point of mental fatigue based on self-organized criticality, which distinguishes the mental fatigue state during driving and comprises the following steps:

Step 1: according to the international standard 10-20 EEG electrode placement system, collecting EEG signals in a prolonged simulated driving process of a driver by the 61 electrodes in FIG. 2, and simultaneously recording the driving behavior data of lane position variability, following distance and real time speed; and then, conducting data preprocessing on the EEG signals, including removal of 50 Hz power line, band-pass filtering (0.5-30 Hz), downsampling and artifact removal based on independent component analysis.

Step 2: analyzing the dynamic functional brain network by using a sliding time window, calculating the correlation coefficients between the EEG data of each channel in the time window to obtain an adjacency matrix, binarizing the adjacency matrix, then constructing a binary functional brain network and extracting statistical characteristics of the network.

Step 3: deducing the avalanche dynamics of mental fatigue on the dynamic functional brain network, constructing the self-organized criticality model by particle addition and particle collapse processes, judging whether the brain network has self-organized criticality and detecting the critical state of mental fatigue.

Step 4: inspecting the validity of calibration of the critical point of fatigue based on the self-organized criticality in combination with the driving behavior data.

Referring to FIG. 2, the second step above is described in detail:

(1) The correlation coefficients between the EEG signals of each channel in the sliding time window is calculated through a cross-correlation function to obtain the weighted adjacency matrix C.

(2) To prevent the existence of isolated nodes, threshold processing is conducted on the adjacency matrix C based on the connected graph method. Only after the threshold is exceeded, a connection would be established to obtain a binary adjacency matrix A. The method for calculating the dynamic threshold of the connected graph comprises:

firstly, setting the threshold T as 1, then gradually decreasing the threshold, and calculating the second smallest characteristic value $\lambda_{min}$ of Laplacian matrix L corresponding to the adjacency matrix each time so that the characteristic value is greater than 0, to ensure that the constructed network belongs to the connected graph.

The elements of the Laplacian matrix L are calculated by the formula:

$$L_{ij}=k_i\delta_{ij}-a_{ij}$$

In the formula, $\delta_{ij}$ is a Kronecker function. When i=j, $\delta_{ij}=1$; otherwise; $\delta_{ij}=0$. $k_i$ is defined as the degree of node i. $a_{ij}$ is an element of the adjacency matrix A.

Therefore, the calculated threshold only depends on the correlation coefficients of the matrix.

(3) The functional brain network is established by using the binary adjacency matrix A. If the element $a_{ij}=1$ in the adjacency matrix A, it indicates there is a connection between nodes i and j; otherwise, if $a_{ij}=0$, there is no connection between nodes i and j.

(4) Finally, the statistical characteristics of the brain network are analyzed, and the statistical characteristics of clustering coefficient, characteristic path length and global efficiency are extracted.

Figure 3:
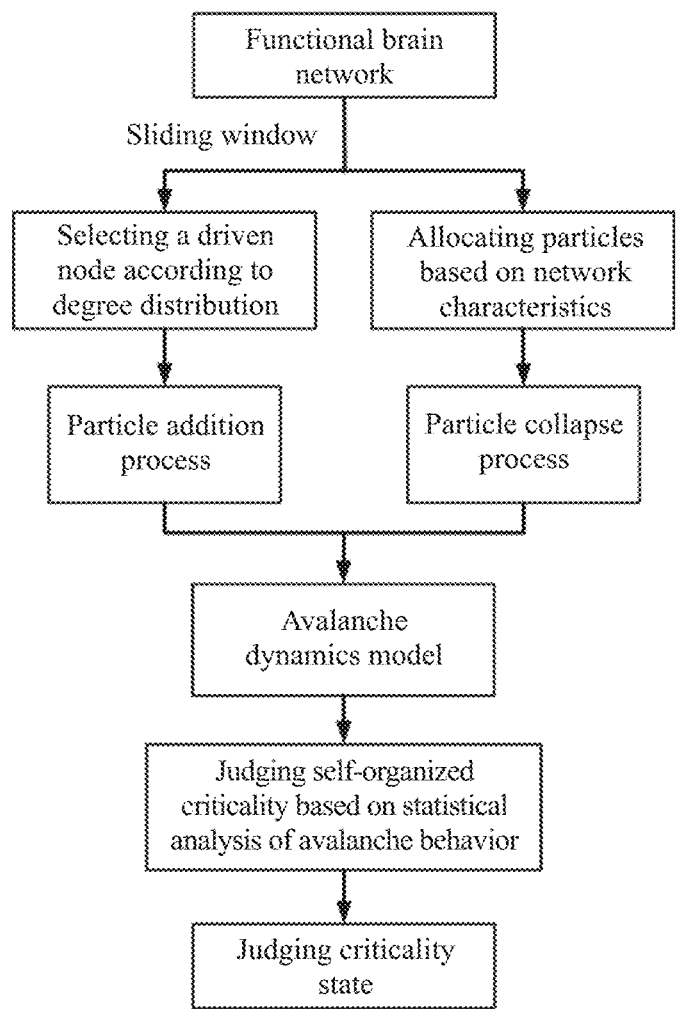
FIG. 3 is a technology roadmap of the avalanche dynamics model in the present invention.

Referring to FIG. 3, the third step is described in detail:

(1) The fatigue index, including clustering coefficient, characteristic path length and global efficiency, of the dynamic functional brain network is calculated to obtain the dynamic characteristics of the brain network. The calculation formula of the fatigue index is as follows:

$$FI=(L-C)/E_{global}$$

In the formula, FI is the fatigue index; L is characteristic path length; C is clustering coefficient; $E_{global}$ is global efficiency. If the FI value is larger, it indicates that the driver is more tired and the ability to maintain alertness is weaker; otherwise, if the FI value is smaller, it indicates that the driver is more vigilant.

Because the fatigue accumulation in a real driving process presents a trend of phasic variation, hierarchical clustering is used to divide the FI into different stages.

(2) A self-organized criticality model is established on the dynamic brain network. Firstly, the avalanche dynamics process is divided into a particle addition process and a particle collapse process. With the assumption of a functional brain network with n nodes, a dynamics variable $h_i$ and a threshold $H_i$ are set on node i, in which the dynamics variable $h_i$ represents the height of its sand pile, and the threshold $H_i$ is the degree value of node i in the brain network. If one or more nodes satisfy h≥H at the same time, the avalanche would occur; on the contrary, if all the nodes satisfy h<H, the morphology of the sand pile is stable. The specific evolution rule is as follows.

The particle addition process:

A grain of sand is added to a driven node i, i.e., $h_i=h_i+1$;

If $h_i<H_i$ holds for all the nodes, the particle addition process is continued; if $h_i \geq H_i$ for the nodes, the morphology of the sand pile is not stable and the particle collapse process is executed.

The particle collapse process:

As long as $h_i \geq H_i$ for any node, the node is not stable and collapses.

All the unstable nodes collapse in a parallel update mode until all the nodes are stable, and an avalanche is thrilled in the whole collapse process.

The particle addition process is continued.

The collapse frequency of the self-organized criticality model established based on the functional brain network can be calculated according to the particle addition process and the particle collapse process, and then the avalanche scale of the dynamic functional brain network can be counted.

(3) In the self-organized criticality model, the self-organized criticality is judged based on whether the distribution of the avalanche scale satisfies the power law distribution condition. The avalanche scale at each stage is calculated. The avalanche scale is set as S and the occurrence probability of the corresponding avalanche scale is set as p(S). A scatter diagram of log-log coordinates is drawn, and data points are used to perform linear regression by the least square method to obtain a fitting straight line and a determination coefficient. The determination coefficient is used to judge whether the logarithm of the avalanche scale S and probability p(S) at each stage has "power" law. Finally, in the embodiments, the logarithm of the avalanche size S and probability p(S) at each stage is judged to have the "power" law, which reflects the self-organized criticality. Therefore, the complex functional brain network has the self-organized criticality.

(4) The maximum avalanche scale at each stage is extracted and analyzed according to the distribution law of the avalanche behaviors on the dynamic functional brain network. At the maximum avalanche scale, the dynamic functional brain network has sparse connections and weak ability to deal with information, which is very easy to lead to driver errors. The maximum avalanche scale is the critical point of fatigue, and the critical point is calibrated in the FI.

The fourth step 4 above is described in detail as follows:

(1) The embodiment involves three types of driving behavior data, i.e., lane position variability distance, following distance and real time speed, and each data can reflect the driving state of the driver. Therefore, the behavior data are fused to obtain the "FI" of the driving behaviors, so as to simplify the verification of calibration for the critical point of fatigue. However, the amplitudes of the three types of driving behavior data are quite different. In order to eliminate the effect of the differences on the "FI" of the driving behaviors, the behavior data is first normalized based on Z-score, and then is fused.

(2) Driving behavior signals are usually aperiodic signals and have uncertainty, but have certain statistical laws. In order to better measure the changes of driving behaviors in the prolonged driving process, the sliding time window is used to extract characteristic parameters of the behavior data, including mean, standard deviation and sample entropy. The mean can reflect the change trend of the driving behaviors; the standard deviation can reflect the smoothness of driving; and the sample entropy is utilized to describe the disorder degree in the driving behaviors.

(3) The characteristic changes of the behavior data near the critical point at each stage are concerned, and the maximum values are marked, so as to detect whether abnormal driving behaviors occur near the critical points.

The above describes the basic principle, main features and advantages of the present invention, but it is not limited to the above embodiments. All technical solutions that belong to the idea of the present invention are included within its protection scope. It should be pointed out that, several improvements and replacements made by those skilled in the art without departing from the spirit of the present invention shall also be considered to be within the protection scope of the present invention.

The invention claimed is:

1. A calibration method for a critical point of mental fatigue based on self-organized criticality, comprising the following steps:

step 1: according to an international standard 10-20 electroencephalograph (EEG) electrode placement system, collecting EEG signals in an operation process, simultaneously collecting operation behavior data and conducting data preprocessing on the EEG signals;

step 2: constructing a dynamic functional brain network by using a sliding time window, and analyzing statistical characteristics of the dynamic functional brain network;

wherein analysis of the dynamic functional brain network comprises:
  calculating correlation coefficients between the EEG signals of channels in the sliding time window to obtain an adjacency matrix;
  establishing a weighted brain network with EEG electrodes as nodes and adjacency matrix elements as edges;
  calculating a maximum threshold that makes the weighted brain network become a connected graph, and binarizing an adjacency matrix to establish a binary brain network;
  analyzing statistical characteristics of the binary brain network, and extracting statistical characteristics of a clustering coefficient, characteristic path length and global efficiency;

step 3: deducing avalanche dynamics of mental fatigue on the dynamic functional brain network, constructing a self-organized criticality model, judging whether the dynamic functional brain network has self-organized criticality and detecting a critical state of mental fatigue;

wherein detection of the critical state of mental fatigue based on the self-organized criticality model comprises:
  integrating the clustering coefficient, the characteristic path length and the global efficiency, and calculating a fatigue index of the dynamic functional brain network to obtain dynamic characteristics of the brain network;

wherein a calculation formula of the fatigue index is as follows $$FT=(L-C)/E_{global}$$

wherein in the formula, F is the fatigue index; L is the characteristic path length; C is the clustering coefficient, $E_{global}$ is the global efficiency;

adding particles to the nodes of the brain network according to degree distribution, and increasing a height of the nodes by 1 after adding the particles;

setting a collapse height threshold of the nodes to be the same as a degree of the nodes, and judging a collapse;

recording a stability of the nodes after the collapse as an avalanche, and deducing the avalanche dynamics;

detecting whether the dynamic functional brain network has self-organized criticality based on that an avalanche behavior of self-organized criticality has "power law" distribution;

calibrating a self-organized critical point by using the "power law" distribution law of the avalanche behavior;

step 4: inspecting a validity of calibration of the critical point of mental fatigue based on the self-organized criticality in combination with the operation behavior data of the operation process; and realizing inspection of the calibration validity of the fatigue critical point through behavior data characteristic extraction, and judging whether behavior data characteristic outliers appear near the critical point.

2. The calibration method for the critical point of mental fatigue according to claim 1, wherein for the behavior data characteristic extraction, an analysis algorithm comprises:

standardizing the behavior data based on Z-score;

fusing the behavior data by a weighted average method; and calculating the mean, standard deviation and sample entropy of the behavior data as characteristic values.

* * * * *